(12) United States Patent
Craige, III et al.

(10) Patent No.: US 6,993,395 B2
(45) Date of Patent: Jan. 31, 2006

(54) SKIN-APPLIED ELECTRODE PADS

(75) Inventors: David N. Craige, III, Attleboro, MA (US); Michael R. Dupelle, Attleboro, MA (US); Sheldon S. White, Brookline, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 10/465,020

(22) Filed: Jun. 19, 2003

(65) Prior Publication Data
US 2004/0260376 A1    Dec. 23, 2004

(51) Int. Cl.
| A61N 1/00 | (2006.01) |
| A61N 1/04 | (2006.01) |
| A61N 1/05 | (2006.01) |
| A61N 1/06 | (2006.01) |

(52) U.S. Cl. .................. 607/142; 607/152; 600/393
(58) Field of Classification Search ............... 607/142, 607/148, 152, 153, 5; 600/393; 604/20; 206/210, 701
See application file for complete search history.

(56) References Cited

U.S. PATENT DOCUMENTS

| 2,699,779 | A | * | 1/1955 | Lustig .................... 604/307 |
| 4,082,086 | A | * | 4/1978 | Page et al. ............... 600/391 |
| 4,166,465 | A | * | 9/1979 | Esty et al. ................ 606/32 |
| 4,248,247 | A | * | 2/1981 | Ware et al. ............... 607/152 |
| 4,722,761 | A | * | 2/1988 | Cartmell et al. ........... 156/242 |
| 4,779,630 | A | * | 10/1988 | Scharnberg et al. ........ 607/142 |
| 5,150,708 | A | * | 9/1992 | Brooks .................... 607/142 |
| 5,352,315 | A | * | 10/1994 | Carrier et al. ............ 156/267 |
| 5,368,581 | A | * | 11/1994 | Smith et al. ............. 604/290 |
| 5,645,527 | A | * | 7/1997 | Beck ...................... 604/20 |
| 5,827,184 | A | * | 10/1998 | Netherly et al. .......... 600/372 |
| 6,019,877 | A |  | 2/2000 | Dupelle et al. ......... 204/196.11 |
| 6,170,653 | B1 | * | 1/2001 | Panzner .................. 206/210 |
| 6,223,088 | B1 | * | 4/2001 | Scharnberg et al. ....... 607/142 |
| 6,603,318 | B2 | * | 8/2003 | Hansen et al. ........... 324/689 |
| 2002/0117408 | A1 | * | 8/2002 | Solosko et al. .......... 206/210 |

OTHER PUBLICATIONS

U.S. Appl. No. 10/608,999, "Medical Electrodes with Long Storage Life" filed Jun. 7, 2003, pending.
U.S. Appl. No. 10/067,475, "Medical Electrodes" filed Feb. 4, 2002, abandoned.

* cited by examiner

*Primary Examiner*—Jeffrey R. Jastrzab
(74) *Attorney, Agent, or Firm*—Fish & Richardson P.C.

(57) ABSTRACT

Electrodes are provided, for example including: (a) a first electrode component including a conductive skin-contacting element, and (b) a second electrode component including a thin electrical conductor. The first and second electrode components may be positioned during storage of the electrode so that the conductive skin-contacting element is not in contact with the thin electrical conductor, and configured so that they can be brought into contact prior to use of the electrode with a surface of the conductive skin-contacting element in contact with a surface of the thin electrical conductor.

37 Claims, 9 Drawing Sheets

SKIN-APPLIED ELECTRODE PADS

TECHNICAL FIELD

This invention relates to skin-applied electrode pads, e.g., for use with defibrillators.

BACKGROUND

Skin-applied electrode pads are well known for use in medical applications such as cardiac pacing, ECG monitoring, and defibrillation. Typically, these electrode pads are attached to a wire lead or cable that is attached at its opposite end to the connector of a medical device or medical device instrumentation. Electrode pads generally include an electrode, e.g., a conductor such as a thin layer of tin or another metal, resting on a foam backing. The electrode typically is covered with a conductive gel that contacts a patient's skin and electrically connects the electrode to the patient, and the electrode pad includes a ring of adhesive surrounding the conductive gel to adhere the electrode to the patient's skin.

For one or more reasons, e.g., to prevent the adhesive gel from drying out, to maintain the electrodes in a sanitary condition, and to cover the adhesive until a caregiver is ready to adhere the electrode to the patient, a release sheet, e.g., a plastic cover, is positioned over the adhesive and/or conductive gel of each electrode.

To use the electrode pads, a caregiver connects the wire leads to an appropriate medical device such as a defibrillator (if they are not pre-connected), removes the release sheets from the electrode pads, and applies the electrode pads to the patient.

Electrodes for use with external defibrillators, such as public access defibrillators (PADs) and other types of automated external defibrillators (AEDs) may be stored for long periods of time, possibly at elevated temperatures, for example in public buildings and emergency vehicles.

Storage may damage the electrode, often rendering it inoperable, due to corrosion of the conductor due to contact of the conductor with the conductive gel. If the electrode is unusable at the time that a caregiver needs to apply the electrode to a patient, the patient's life can be jeopardized or lost due to delay in finding a useable electrode.

SUMMARY

The present invention features electrodes that exhibit excellent shelf life, i.e., the electrodes can be stored for extended periods without significant corrosion of the conductor.

In one aspect, the invention features an electrode configured to be attached to a patient's skin, the electrode including (a) a first electrode component including a conductive skin-contacting element, and (b) a second electrode component including a thin electrical conductor, the first and second electrode components being positioned during storage of the electrode so that the conductive skin-contacting element is not in contact with the thin electrical conductor, and being configured so that they can be brought into contact prior to use of the electrode with a surface of the conductive skin-contacting element in contact with a surface of the thin electrical conductor.

Some implementations include one or more of the following features. The electrode may be configured to be used with a defibrillator, ECG or ESU machine, pacing machine, or other stimulating or monitoring device that requires body-contacting electrodes. For example, the electrode may be configured to acquire data indicative of the patient's heart rhythm and to deliver a defibrillating shock if appropriate.

The electrode components may be positioned during storage so that the surfaces that are brought into contact prior to use of the electrode face each other. The surfaces that face each other may be separated by a barrier such as a release liner.

Alternatively, the electrode components may be positioned during storage so that the surfaces that are brought into contact prior to use of the electrode lie in the same plane. The surfaces that are brought into contact prior to use may be adhered to a release sheet, and the electrode may be configured so that the electrode components draw together when the electrode components are peeled from the release sheet prior to use.

In a further alternative construction, the electrode components may be positioned during storage so that the surfaces that are brought into contact prior to use of the electrode face away from each other. The electrode components may be configured to pass through a 180 degree bend when they are brought into contact. For example, the surfaces that are brought into contact may be adhered to opposed walls of a container during storage. Surfaces opposite to the surfaces that are brought into contact may be adhered to outer surfaces of a package, and the electrode may further include a release paper covering the surfaces that are brought into contact.

The conductive skin-contacting element may include a conductive gel. The first electrode component may include a support, e.g., a foam material, and the conductive gel may be positioned on the support. The first electrode component may have a skin-contacting surface configured to be attached to the patient's skin and an opposite surface, the skin-contacting surface including an exposed portion of the conductive skin-contacting element. The second electrode component may include a support, e.g., a foam sheet material, and the conductor may be positioned on the support. At least one of the first and second electrode components may carry an adhesive to bond the first and second electrode components together after they are brought into contact.

In another aspect, the invention features an electrode product including: (a) an electrode configured to be attached to a patient's skin, and (b) a packaging member. The electrode includes a first electrode component including a conductive skin-contacting element, and a second electrode component including a thin electrical conductor. The first and second electrode components are positioned during storage of the electrode so that the conductive skin-contacting element is not in contact with the thin electrical conductor, and are configured so that the electrode components can be brought into contact prior to use of the electrode with a surface of the conductive skin-contacting element in contact with a surface of the thin electrical conductor. The packaging member is configured to maintain the first and second electrode components separated during storage of the electrode, and to allow the electrode components to be released from the packaging member and brought into contact with each other prior to use of the electrode.

Some implementations may include one or more of the following features. The first and second electrode components may be arranged side-by-side on a surface of the packaging member. The packaging member may include a sheet material, e.g., a release liner. The first and second electrode components may be adhered to the sheet material with the surfaces that are brought into contact prior to use facing the sheet material. The electrode may include a central tab configured to allow the user to peel the electrode components from the sheet material. The packaging member may include a box to which a portion of the sheet material is adhered, the box having an opening through which the electrode can be drawn as the electrode is removed from the packaging member. The opening may be configured to draw the electrode components together as the electrode is removed from the box. Alternatively, the first and second electrodes may be positioned so that the conductive skin-contacting element and the thin electrical conductor face away from each other during storage. Surfaces of the electrode components opposite to the surfaces that are brought into contact are adhered to an outer surface of the packaging member. For example, the packaging member may include two portions arranged in a clamshell configuration. In another alternative configuration, the first and second electrodes may be positioned so that the conductive skin-contacting element and the thin electrical conductor face towards each other.

Other features and advantages of the invention will be apparent from the detailed description and drawings, and from the claims.

DESCRIPTION OF DRAWINGS

Like reference symbols in the various drawings indicate like elements.

DETAILED DESCRIPTION

Figure 1:
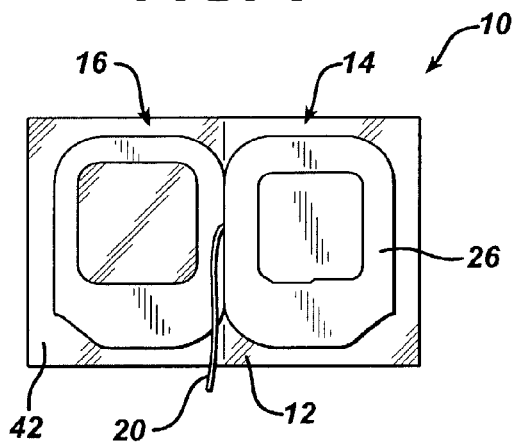
FIG. 1 is a front plan view of an electrode product according to one embodiment of the invention, including an electrode during storage and packaging for the electrode. The packaging is shown as transparent, for clarity.

Referring to FIG. 1, an electrode product 10 includes a release liner 12, and, mounted on the release liner, first and second electrode components 14 and 16. The electrode components are positioned side-by-side during storage, as shown in FIG. 1, but are brought together to form a single electrode assembly 18 (FIG. 1A) prior to use. The manner in which the electrode components are brought together will be discussed in detail below. A cable 20 is provided to connect the electrode 18 to a medical device (not shown), e.g., the control box of a defibrillator.

Figure 1A:
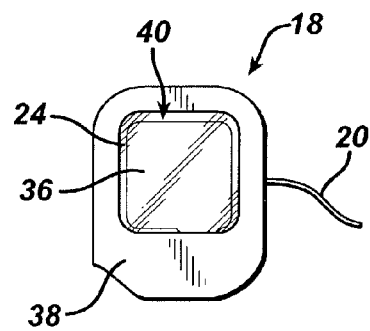
FIG. 1A is a front plan view of the electrode shown in FIG. 1, ready for use.
Figure 1B:
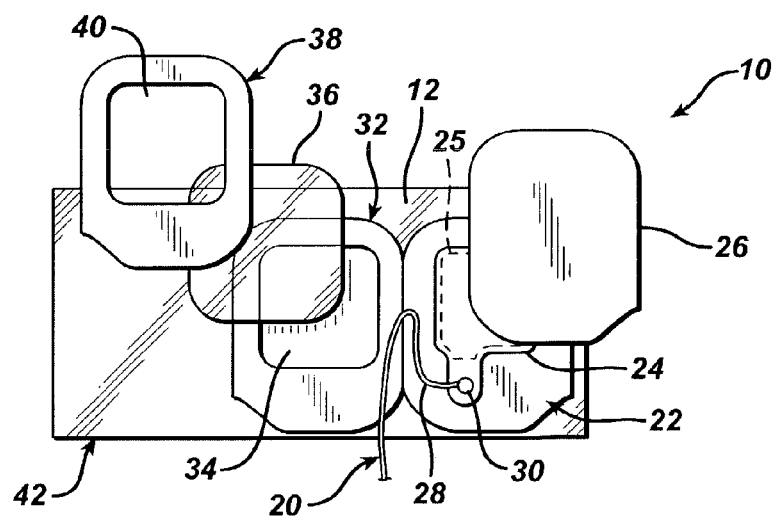
FIG. 1B is an exploded view of the electrode product shown in FIG. 1.

Referring to FIGS. 1 and 1B, the electrode components include the following components. The first electrode component 14 includes a support 22 defining a central opening 25, a thin metallic conductor 24, e.g., tin, positioned so that at least a portion of the metallic conductor directly contacts the release liner 12, and a covering 26. The support and covering are sealed together around their facing edges, e.g., by an adhesive, holding the metallic conductor 24 in place. The support and covering may be formed of a compliant material, e.g., a foam sheet material such as a closed cell polyethylene foam, to provide resiliency and compliance to the skin surface of a patient. A portion 28 of the cable 20 is sandwiched between the support and covering, for reasons that will be discussed below. Cable 20 is electrically connected to metallic conductor 24 by a ring and socket connector 30. The support generally includes a pressure sensitive adhesive on its surface that is adjacent the release liner 12, to adhere the support to the release liner.

The second electrode component 16 includes a support 32 defining a central opening 34, a conductive skin-contacting element 36, e.g., a solid electrolyte gel, and a skin-contacting cover 38 defining an opening 40 to allow the skin-contacting element 36 to contact the patient's skin when the electrode is in use. The central opening 34 allows the skin-contacting element to directly contact the conductor 24 when the electrode is assembled as shown in FIG. 1A. Support 32 and skin-contacting cover 38 may be formed of a compliant material as discussed above. Generally, support 32 includes a pressure sensitive adhesive on its surface that is adjacent the release liner 12, to adhere the support to the release liner. Cover 38 also includes a pressure sensitive adhesive, to adhere the electrode to the patient's skin during use. To protect this adhesive, a portion 42 of the release liner 12 is folded over the cover 38 to serve as a release liner during storage of the electrode.

Figure 1C:
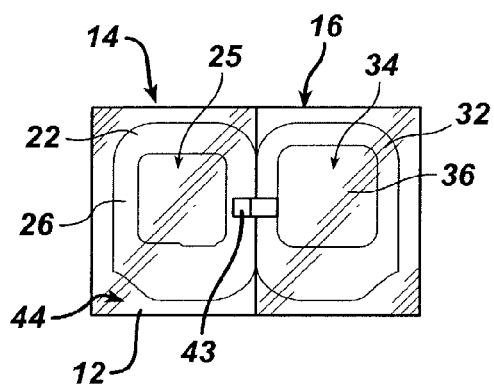
FIG. 1C is a rear plan view of the electrode product shown in FIG. 1.
Figure 2:
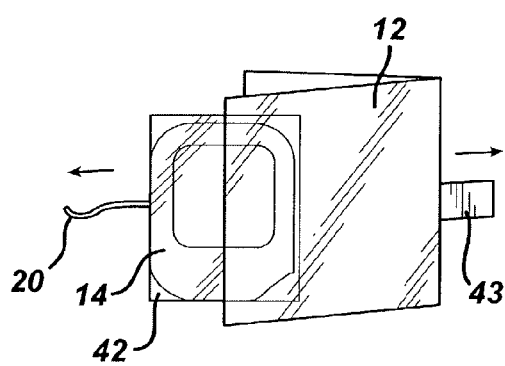
FIGS. 2–2A are diagrammatic perspective views.
Figure 2A:
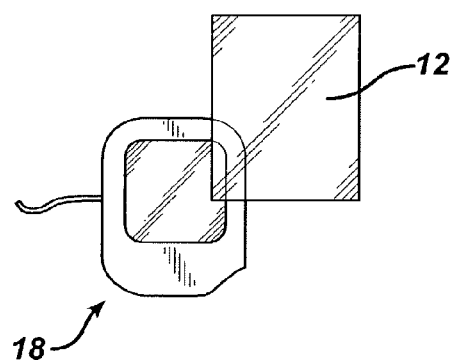
Figure 3:
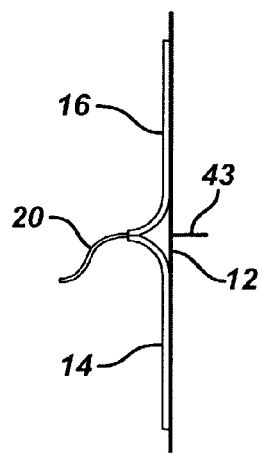
FIGS. 3–3C are diagrammatic side views, respectively, showing stages in the removal of the electrode of FIG. 1 from its packaging.
Figure 3A:
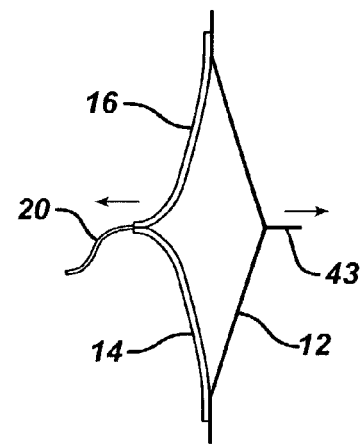
Figure 3B:
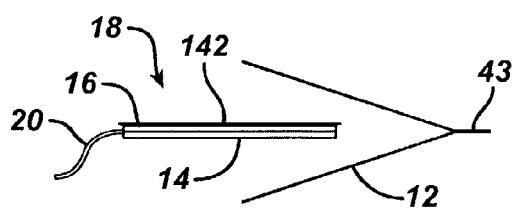

As shown in FIG. 1C, a tab 43 extends from the back surface 44 of the release liner 12 (i.e., the surface opposite the surface to which the electrode components are adhered). This tab allows a user to grasp tab 43 in one hand and cable 20 in the other hand, and pull the release liner 12 off of the electrode components as shown in FIGS. 2–2A and 3–3C. As shown in FIGS. 3–3B, as the release liner 12 is peeled off of the electrode components, the electrode components draw together, so that they contact and adhere to each other. Thus, the user can generally assemble the two electrode components without letting go of cable 20 and tab 43. After the release liner has been completely removed, the user may press the edges of the electrode components together to ensure a good seal between the electrode components.

Figure 3C:
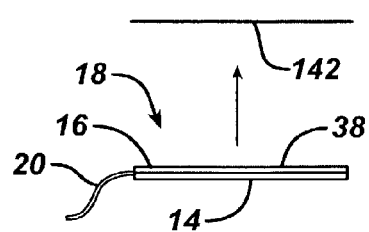

As indicated diagrammatically in FIG. 3C, prior to applying the electrode 18 to a patient, the user removes the release sheet 142 (shown in FIG. 3C as a separate sheet) to expose the pressure sensitive adhesive on skin-contacting cover 38. The user can then adhere the electrode to the patient's chest using this adhesive. Alternatively, if the release sheet is a folded-over portion of the release liner, as shown in FIG. 1 and discussed above, the release sheet would be removed by unfolding the release liner prior to peeling the release liner off of the electrode components.

Figure 4:
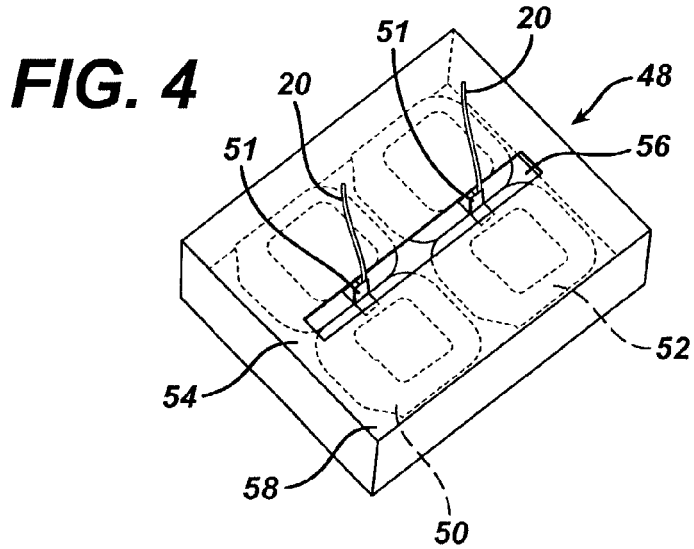
FIG. 4 is a perspective view of an electrode product according to another embodiment of the invention, with the packaging shown as transparent for clarity.
Figure 5:
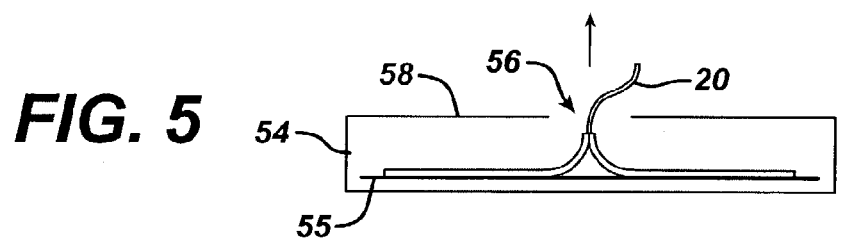
FIGS. 5–5B are diagrammatic side views showing stages in the removal of the electrode of FIG. 4 from its packaging.
Figure 5A:
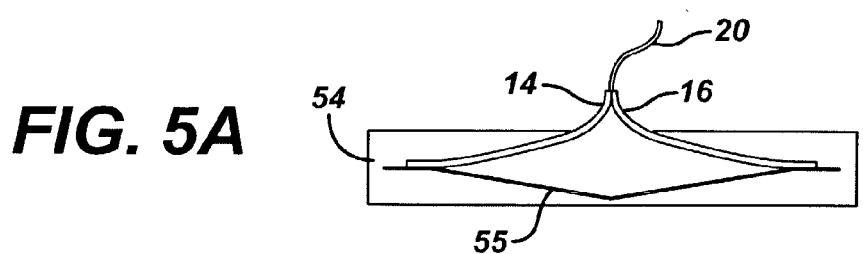
Figure 5B:
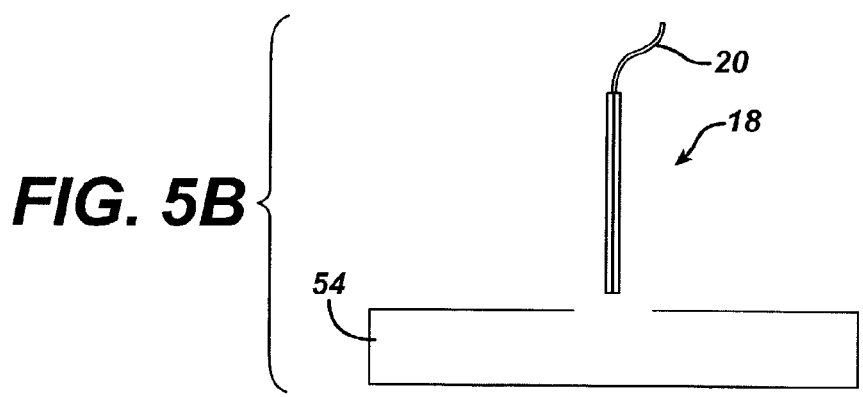

FIG. 4 shows an electrode product 48 that is similar to that shown in FIG. 1 in that the electrode components are arranged side-by-side on a flat substrate. In the product shown in FIG. 4, two stored electrodes 50, 52 are arranged in a box 54 (shown as transparent). Each of the stored electrodes includes two separated electrode components as discussed above. The electrode components are adhered to an initially flat, flexible backing 55 (FIG. 5) within the box. The cords 20 of the electrodes extend upwards through a slot 56 in the cover 58 of the box. As shown in FIGS. 5–5B, each electrode can be removed from the box by pulling upward on cord 20 to peel the two electrode components off of the backing 55 (FIG. 5A). The backing 55 is adhered to the box along the center, to allow the backing to flex so that the adhesive on the electrode components is subjected to a peel force rather than a shearing force. As shown in FIG. 4, tabs 51 are provided adjacent to cords 20, to allow the user to grip the cord 20, tab 51, or both, when peeling the electrode components off the backing and thereby maximize leverage and facilitate removal.

Figure 6:
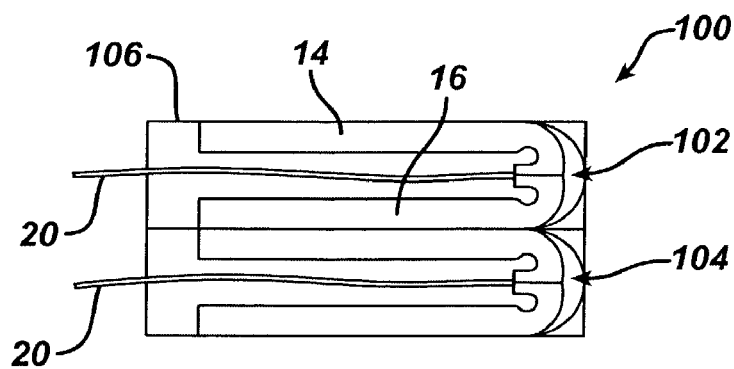
FIG. 6 is a side view of an electrode product according to another embodiment of the invention.
Figure 6A:
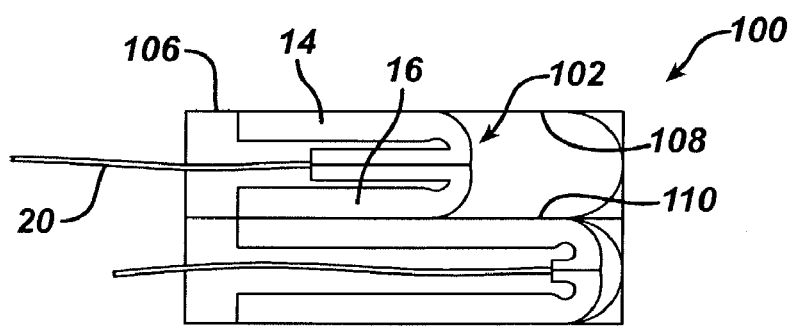
FIGS. 6A–6B are diagrammatic side views showing stages in the removal of one of the pair of electrodes shown in FIG. 6 from its packaging.
Figure 6B:
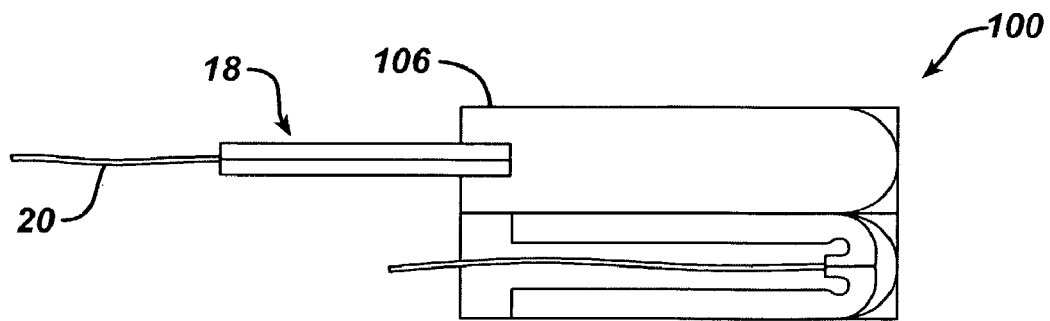

An alternate embodiment, in which the electrode components are arranged back-to-back, i.e., with their surfaces that will form the outside of the assembled electrode facing each other, is shown in FIG. 6. In the electrode product 100 shown in FIG. 6, two stored electrodes 102, 104 are provided in a multi-compartment box 106. Each compartment includes a pair of opposed walls 108, 110, to which the electrode components are adhered. The electrode components are attached to each other at the midpoint of the electrode, where the cable 20 exits the electrode. As shown in FIGS. 6A and 6B, an electrode 18 is assembled from one of the stored electrodes by pulling the cable 20 to peel the electrode components 14, 16, off of walls 108, 110. As the electrode components are peeled off of the walls, they are drawn towards and adhere to each other, forming assembled electrode 18 (FIG. 6B).

Figure 7:
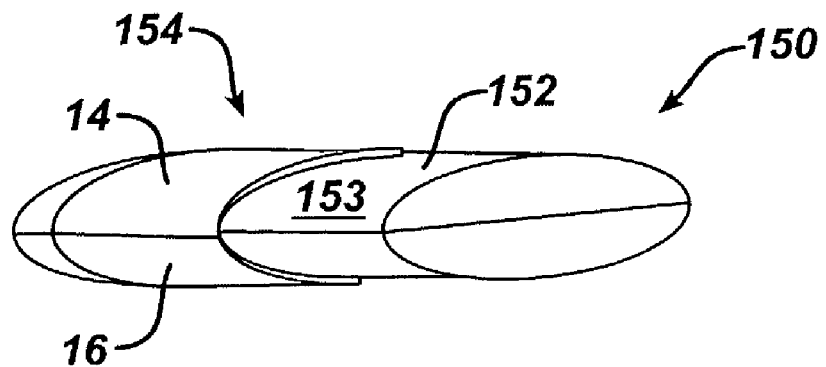
FIG. 7 is a perspective view of an electrode product according to another embodiment of the invention.
Figure 7A:
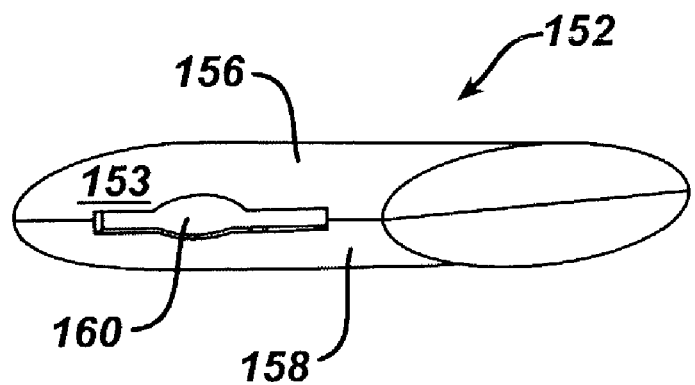
FIG. 7A is a perspective view of the packaging shown in FIG. 7, with the electrode removed.
Figure 8:
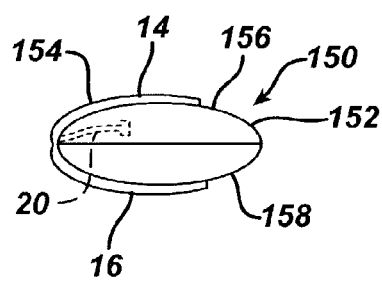
FIGS. 8–8E are diagrammatic side views showing stages in the removal of the electrode of FIG. 7 from its packaging.
Figure 8A:
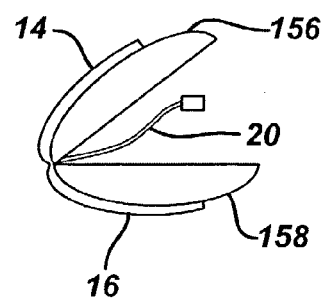
Figure 8B:
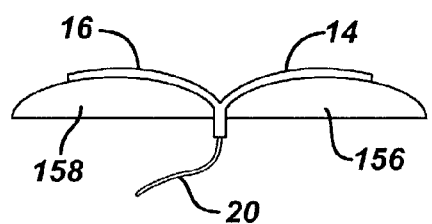
Figure 8C:
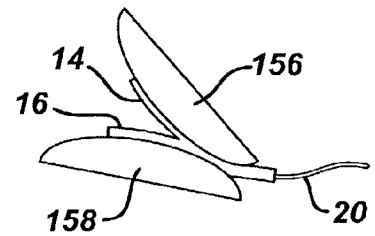

Another embodiment in which the electrode components are arranged back-to-back is shown in FIGS. 7 and 8. In this embodiment, electrode product 150 includes a tubular backing 152 and a stored electrode 154 including electrode components 14, 16, adhered to an outer surface 153 of the tubular backing. As shown in FIG. 7A, tubular backing 152 consists of two halves 156, 158, disposed in a clamshell arrangement, and includes an opening 160 through which the cable 20 of the stored electrode 154 can be inserted when the electrode components are adhered to surface 153.

Figure 8D:
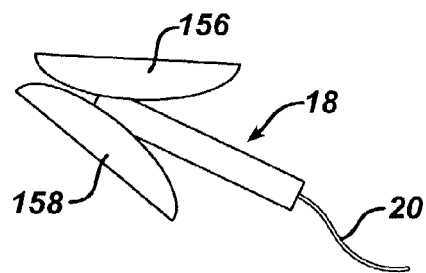
Figure 8E:
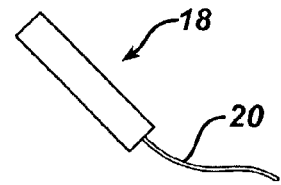

Stored electrode 154 is removed from tubular backing 152 as shown in FIGS. 8A–8E. First, the tubular backing 152 is opened by separating the two halves 156, 158 (FIG. 8A), exposing cable 20. The user then pulls on cable 20, causing the two halves to rotate about the point at which the cable 20 exits the electrode (FIGS. 8B, 8C), bringing the two electrode components together (FIG. 8D). Once the electrode components have adhered to each other, forming electrode 18, the halves 156, 158 of the tubular backing 152 can be discarded (FIG. 8E). A release sheet (not shown) may be provided to protect the exposed adhesive on the electrode components. The electrode product 150 may be sealed in a pouch or other container to prevent drying out of the electrolyte gel and maintain cleanliness of the stored electrode.

Figure 9:
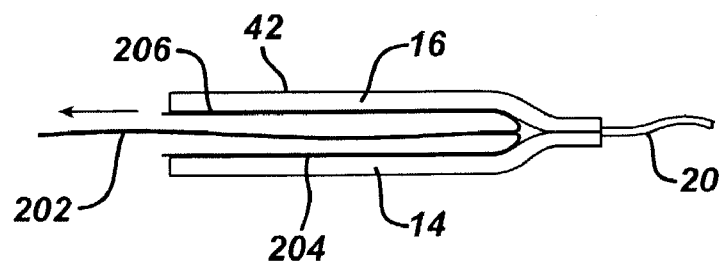
FIG. 9 is a side view of an electrode product according to another embodiment of the invention.
Figure 9A:
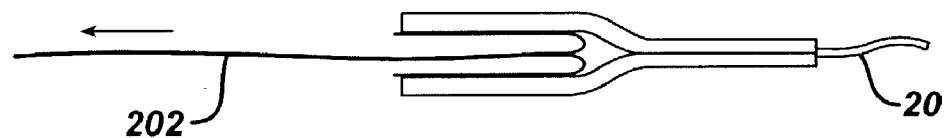
FIGS. 9A–9C are diagrammatic side views showing stages in the removal of the electrode of FIG. 9 from its packaging.
Figure 9B:
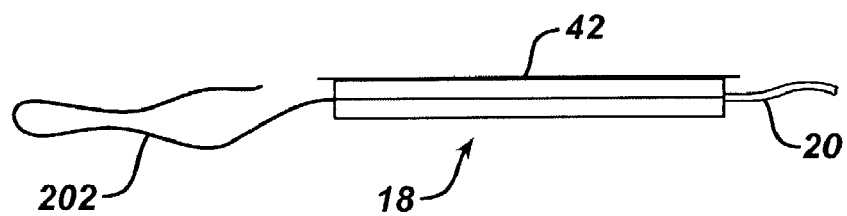
Figure 9C:
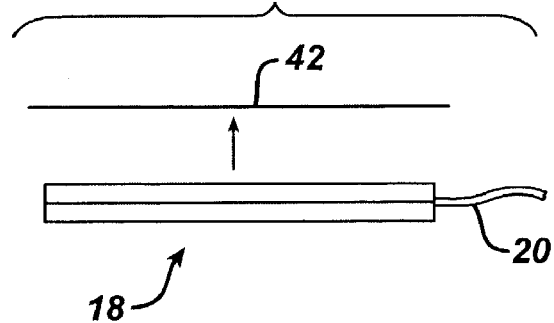

In another alternate embodiment, shown in FIG. 9, electrode product 200 includes two electrode components stored face-to-face, i.e., with their surfaces that will be adhered together in the finished electrode facing each other during storage. In this embodiment, a release liner 202 is positioned between the two electrode components to separate them during storage. Release liner 202 includes two U-shaped portions 204, 206, to allow it to be easily peeled from between the two electrode components as shown in FIG. 9A.

Figure 10:
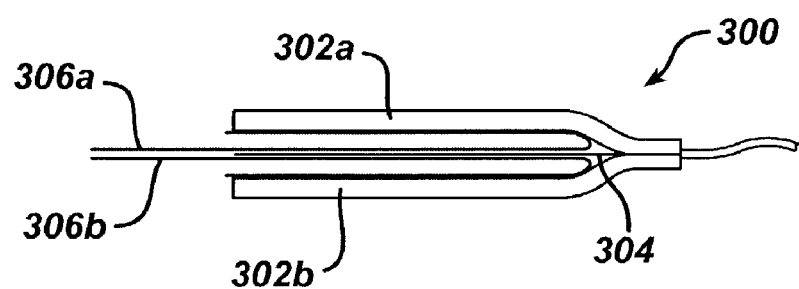
FIGS. 10 and 10A are diagrammatic side views showing an electrode product according to another embodiment of the invention, as stored and during removal of the electrode from its packaging, respectively.
Figure 10A:
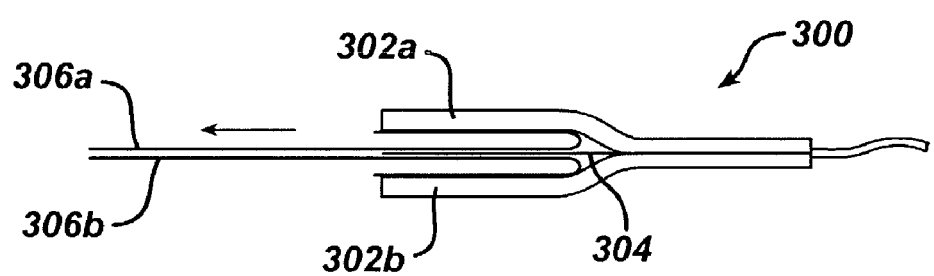

In another embodiment, shown in FIGS. 10 and 10A, electrode product 300 includes two electrode components 302a, 302b, stored face-to-face, with a double-faced adhesive sheet 304 positioned between them. In this case, the electrode components 302a and 302b do not include an adhesive coating, but are instead adhered to each other by the double-faced adhesive sheet 304. Release liners 306a, 306b are interposed between each face of the adhesive sheet 304 and the adjacent electrode component, to prevent the electrode components from adhering to each other prematurely and to provide a barrier between the electrode components.

The release sheets described above may be a release-coated paper, a plastic sheet material (including non-polymeric films having the properties of plastics), a polymeric film, or any other suitable sheet material having release properties sufficient to release from the gel layer and adhesive.

Other embodiments are within the scope of the following claims.

For example, the electrode 18 may have any desired shape and size, including square, circular, or oval.

The conductor may be metallic or non-metallic.

The adhesive ring may be formed of a non-conductive or conductive adhesive, and the adhesive may be provided in any other desired shape or configuration.

Moreover, the electrode 18 may include text or other indicia to help a caregiver locate the electrode, e.g., as disclosed in U.S. Ser. No. 09/794,320, the disclosure of which is incorporated herein by reference.

What is claimed is:

1. An electrode configured to be attached to a patient's skin, the electrode comprising:
    a first electrode component including at least one conductive skin-contacting layer configured to be sufficiently flexible to conform to the patient's body and to deliver current to the patient's skin across a current delivery area; and
    a second electrode component including at least one thin electrical conductor layer configured to be sufficiently flexible to conform to the patient's body and to deliver current to the skin contacting layer across approximately the current delivery area;
    the first and second electrode components being positioned during storage of the electrode so that the conductive skin-contacting layer is not in contact with the thin electrical conductor layer, and
    the first and second electrode components being configured so that they can be brought into contact prior to use of the electrode with a surface of the conductive skin-contacting layer in contact with a surface of the thin electrical conductor layer.

2. The electrode of claim 1 wherein the electrode is configured to be used with a defibrillator, ECG or ESU machine, pacing machine, or other stimulating or monitoring device that requires body contacting electrodes.

3. The electrode of claim 2 wherein the electrode is configured to acquire data indicative of the patient's heart rhythm and to deliver a defibrillating shock if appropriate.

4. The electrode of claim 1 wherein the electrode components are positioned during storage so that the surfaces that are brought into contact prior to use of the electrode face each other.

5. The electrode of claim 4 wherein the surfaces that are brought into contact with each other are separated by a barrier during storage.

6. The electrode of claim 5 wherein the barrier comprises a release sheet.

7. The electrode of claim 1 wherein the electrode components are positioned during storage so that the surfaces that are brought into contact prior to use of the electrode lie in the same plane.

8. The electrode of claim 7 wherein the surfaces that are brought into contact prior to use are adhered to a release sheet.

9. The electrode of claim 8 wherein the electrode is configured so that the electrode components draw together when the electrode components are peeled from the release sheet prior to use.

10. The electrode of claim 1 wherein the electrode components are positioned during storage so that the surfaces that are brought into contact prior to use of the electrode face away from each other.

11. The electrode of claim 10 wherein the electrode components are configured to pass through a 180 degree bend when they are brought into contact.

12. The electrode of claim 10 or 11 wherein the surfaces that are brought into contact are adhered to opposed walls of a container during storage.

13. The electrode of claim 10 wherein surfaces opposite to the surfaces that are brought into contact are adhered to outer surfaces of a package, and the electrode further comprises a release paper covering the surfaces that are brought into contact.

14. The electrode of claim 1 wherein the conductive skin-contacting layer comprises a conductive gel.

15. The electrode of claim 14 wherein the skin contacting layer comprises a support and the conductive gel is positioned on the support.

16. The electrode of claim 15 wherein the support comprises a foam sheet material.

17. The electrode of claim 1 wherein the skin contacting layer has a skin-contacting surface configured to be attached to the patient's skin and an opposite surface, the skin-contacting surface comprising an exposed portion of the conductive skin-contacting layer.

18. The electrode of claim 1 wherein the second electrode component comprises a support and the conductor layer is positioned on the support.

19. The electrode of claim 18 wherein the support comprises a foam sheet material.

20. The electrode of claim 1 wherein at least one of the first and second electrode components carries an adhesive to bond the first and second electrode components together after they are brought into contact.

21. An electrode product comprising:
    (a) an electrode configured to be attached to a patient's skin, the electrode comprising:
    a first electrode component including at least one conductive skin-contacting layer configured to be sufficiently flexible to conform to the patient's body and to deliver current to the patient's skin across a current delivery area; and
    a second electrode component including at least one thin electrical conductor layer configured to be sufficiently flexible to conform to the patient's body and to deliver current to the skin contacting layer across approximately the current delivery area;
    the first and second electrode components being positioned during storage of the electrode so that the conductive skin-contacting layer is not in contact with the thin electrical conductor layer, and
    the first and second electrode components being configured so that they can be brought into contact prior to use of the electrode with a surface of the conductive skin-contacting layer in contact with a surface of the thin electrical conductor layer; and
    (b) a packaging member configured to maintain the first and second electrode components separated during storage of the electrode, and to allow the electrode components to be released from the packaging member and brought into contact with each other prior to use of the electrode.

22. The product of claim 21 wherein the first and second electrode components are arranged side-by-side on a surface of the packaging member.

23. The product of claim 22 wherein the packaging member comprises a sheet material.

24. The product of claim 23 wherein the first and second electrode components are adhered to the sheet material with the surfaces that are brought into contact prior to use facing the sheet material.

25. The product of claim 24 wherein the electrode includes a central tab configured to allow the user to peel the electrode components from the sheet material.

26. The product of claim 24 wherein the packaging member comprises a box to which a portion of the sheet material is adhered, the box having an opening through which the electrode can be drawn as the electrode is removed from the packaging member.

27. The product of claim 26 wherein the opening is configured to draw the electrode components together as the electrode is removed from the box.

28. The product of claim 21 wherein the first and second electrodes are positioned so that the conductive skin-contacting layer and the thin electrical conductor face away from each other during storage.

29. The product of claim 28 wherein the electrode components are configured to pass through a 180 degree bend when they are brought into contact.

30. The product of claim 28 or 29 wherein the surfaces that are brought into contact are adhered to opposed walls of the packaging member during storage.

31. The product of claim 28 wherein surfaces of the electrode components opposite to the surfaces that are brought into contact are adhered to an outer surface of the packaging member.

32. The product of claim 31 wherein the packaging member comprises two portions arranged in a clamshell configuration.

33. The product of claim 32 wherein the outer surface of the packaging member is generally convex.

34. The product of claim 31 wherein the electrode further comprises a release paper covering the surfaces of the electrode component that are brought into contact prior to use.

35. The product of claim 21 wherein the first and second electrodes are positioned so that the conductive skin-contacting layer and the thin electrical conductor layer face towards each other.

36. The product of claim 35 wherein the surfaces that are brought into contact with each other are separated by a barrier during storage.

37. The product of claim 36 wherein the barrier comprises a release sheet.

* * * * *